United States Patent
Cardinali et al.

(10) Patent No.: US 12,128,215 B2
(45) Date of Patent: Oct. 29, 2024

(54) DRUG DELIVERY DEVICE WITH INTEGRATED OPTICAL-BASED GLUCOSE MONITOR

(71) Applicant: Insulet Corporation, Acton, MA (US)

(72) Inventors: Steven Cardinali, Tewksbury, MA (US); David Nazzaro, Groveland, MA (US); Ian McLaughlin, Groton, MA (US)

(73) Assignee: INSULET CORPORATION, Acton, MA (US)

(*) Notice: Subject to any disclaimer, the term of this patent is extended or adjusted under 35 U.S.C. 154(b) by 238 days.

(21) Appl. No.: 17/487,570

(22) Filed: Sep. 28, 2021

(65) Prior Publication Data
US 2022/0096749 A1 Mar. 31, 2022

Related U.S. Application Data

(60) Provisional application No. 63/085,853, filed on Sep. 30, 2020.

(51) Int. Cl.
*A61M 5/172* (2006.01)

(52) U.S. Cl.
CPC ... *A61M 5/1723* (2013.01); *A61M 2205/0238* (2013.01); *A61M 2205/3313* (2013.01); *A61M 2230/201* (2013.01)

(58) Field of Classification Search
CPC ............ A61B 5/14532; A61B 5/1455; A61M 5/1723; A61M 5/14248; A61M 2005/14252; A61M 2205/3313; A61M 2205/0238; A61M 2230/201
See application file for complete search history.

(56) References Cited

U.S. PATENT DOCUMENTS

| | | |
|---|---|---|
| 303,013 A | 8/1884 | Horton |
| 2,797,149 A | 6/1957 | Skeggs |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Tiffany Legette
(74) *Attorney, Agent, or Firm* — GOODWIN PROCTER LLP

(57) ABSTRACT

Embodiments of the present disclosure relate to approaches for more efficiently measuring glucose levels using a wearable drug delivery device. In some embodiments, the wearable drug delivery device may include a needle deployment component including a cannula and an optical conduit deployable into a user, the cannula operable to deliver a liquid drug to the user. The wearable drug delivery device may further include a glucose monitor including an optical sensor, the optical sensor operable to measure a light output received via the optical conduit.

20 Claims, 8 Drawing Sheets

(56) References Cited

U.S. PATENT DOCUMENTS

| | | |
|---|---|---|
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kommerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |

(56) References Cited

U.S. PATENT DOCUMENTS

| | | |
|---|---|---|
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Eong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1* | 10/2002 | Han .................. G01N 33/66 435/14 |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |

(56) References Cited

U.S. PATENT DOCUMENTS

| | | |
|---|---|---|
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0256593 A1* | 10/2010 | Yodfat .............. A61M 5/14248 600/347 |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Anier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |

(56) References Cited

U.S. PATENT DOCUMENTS

| | | |
|---|---|---|
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birthwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0198607 A1* | 7/2015 | Peyser ............... A61B 5/14532 422/69 |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Linteruer et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |

(56) References Cited

FOREIGN PATENT DOCUMENTS

| | | | |
|---|---|---|---|
| WO | 9800193 | A1 | 1/1998 |
| WO | 9956803 | A1 | 11/1999 |
| WO | 0030705 | A1 | 6/2000 |
| WO | 0032258 | A1 | 6/2000 |
| WO | 0172354 | A2 | 10/2001 |
| WO | 2002015954 | A1 | 2/2002 |
| WO | 0243866 | A2 | 6/2002 |
| WO | 02082990 | A1 | 10/2002 |
| WO | 03016882 | A1 | 2/2003 |
| WO | 03039362 | A1 | 5/2003 |
| WO | 03045233 | A1 | 6/2003 |
| WO | 05110601 | A1 | 5/2004 |
| WO | 2004043250 | A1 | 5/2004 |
| WO | 04092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A1 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A2 | 4/2020 |
| WO | 2021011738 | A1 | 1/2021 |

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Aorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPhone App on iOS 11", GoToTags, 11 Sep. 2017, web <https://gototags.com/blog/read-hfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030652, Sep. 25, 2019, 19 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

(56) References Cited

OTHER PUBLICATIONS

International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/en/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for International Patent Application No. PCT/US2021/052372, mailed Jan. 26, 2022, 15 pages.
International Preliminary Report on Patentability in PCT/US2021/052372 mailed on Apr. 13, 2023, 10 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 151 pages.
International Search Report and Written Opinion for the International Patent Application No. PCT/US2021/041954, mailed Oct. 25, 2021, 13 pages.
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
International Search Report and Written Opinion for the International Patent Application No. PCT/US2021051027, mailed Jan. 7, 2022, 16 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. ""Single-Versus Triple-Lumen Central Catheter-Related Sepsis: A Prospective Randomized Study in a Critically Ill Population"" The American Journal of Medicine September 1992vol. 93 p. 277-282.

(56) References Cited

OTHER PUBLICATIONS

Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination Of Haemodialysis Catheter Connections"" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS. 247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips"Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

DRUG DELIVERY DEVICE WITH INTEGRATED OPTICAL-BASED GLUCOSE MONITOR

CROSS-REFERENCE TO RELATED APPLICATIONS

This application claims the benefit to U.S. Provisional Application No. 63/085,853, filed Sep. 30, 2020, the entire contents of which are incorporated herein by reference in their entirety.

TECHNICAL FIELD

The disclosed examples generally relate to medication delivery. More particularly, the disclosed examples relate to techniques, processes, devices or systems for monitoring glucose using an optical-based glucose monitor integrated within a drug delivery device.

BACKGROUND

Wearable drug delivery devices are integrated devices, which combine a fluid reservoir, a pumping mechanism, and a mechanism for inserting an integrated subcutaneous cannula. The wearable drug delivery device is adhesively attached to an infusion site on the patient's skin, and typically does not require the use of a separate infusion or tubing set. Some wearable devices deliver a liquid drug (e.g., insulin) to the patient over a period of time via the cannula. The wearable drug delivery device may wirelessly communicate with a separate controller device, such as a personal diabetes manager (PDM).

Drug delivery devices can be used in conjunction with continuous glucose monitoring (CGM) devices. A CGM provides a substantially continuous estimated blood glucose level through a transcutaneous sensor that measures analytes, such as glucose, in the patient's interstitial fluid rather than their blood. CGM systems typically consist of a transcutaneously-placed sensor, a transmitter and a monitor. Some CGM systems allow a patient or caregiver to insert a single sensor probe under the skin for multiple days. Thus, the patient is only required to perform a single moderately invasive action with a single entry point. The CGM may communicate with the drug delivery device via, e.g., a wireless data communication protocol.

One approach for determining a concentration of glucose in a sample includes the use of an optical sensor, which may be fully implanted under the skin of the patient, remaining in place for up to 90 days in some cases. However, the sensor must be surgically implanted and removed by a qualified health care provider during outpatient procedures, thus increasing risk and inconvenience for the patient.

Accordingly, there is a need for a less invasive method for measuring glucose in a patient using an optical based glucose sensor.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one approach, a wearable drug delivery device may include a needle deployment component including a cannula and an optical conduit deployable into a user, the cannula operable to deliver a liquid drug to the user. The wearable drug delivery device may further include a glucose monitor including an optical sensor, the optical sensor operable to measure a light output received via the optical conduit.

In another approach, a method may include providing a wearable drug delivery device, the wearable drug delivery device having a needle deployment component including a cannula and an optical conduit, the cannula operable to deliver a liquid drug into a user, and a glucose monitor including an optical sensor. The method may further include deploying the cannula and the optical conduit into the user, and detecting, by the optical sensor, a light output received via the optical conduit.

In yet another approach, a wearable drug delivery device may include a needle deployment component including a cannula and an optical conduit coupled together, the cannula operable to deliver a liquid drug into a user. The wearable drug delivery device may further include a glucose monitor including an optical sensor, wherein the optical sensor is operable to measure a light output received via the optical conduit, and wherein the needle deployment component and the glucose monitor are located within a same outer housing.

BRIEF DESCRIPTION OF THE DRAWINGS

In the drawings, like reference characters generally refer to the same parts throughout the different views. In the following description, various embodiments of the present disclosure are described with reference to the following drawings, in which.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of the systems, devices, and methods to those skilled in the art. Each of the systems, devices, and methods disclosed herein provides one or more advantages over conventional systems, devices, and methods.

Embodiments of the present disclosure include a open-loop system, closed-loop system, or hybrid system having a pump and a continuous glucose monitor (CGM) housed together. A mechanism in the pump, such as a needle deployment component, may simultaneously introduce a cannula for liquid drug (e.g., insulin) infusion into tissue of a patient together with one or more optical conduits (e.g., optical fibers) operable with an optical sensor. The cannula and the optical conduit may be coupled together, thus preventing the need of multiple injection mechanisms and additional steps by the patient. In some embodiments, the optical sensor and the optical conduit measure glucose levels of the patient tissue and send information to the pump and/or an external device (e.g., smart phone, smart watch, HCP, etc.) to indicate when glucose levels are too high (hyperglycemia) or too low (hypoglycemia). In some embodiments, the optical conduit and/or the cannula may be coated with a fluorescent material which, when exposed to glucose, produces a small amount of light that is delivered through the optical conduit for measurement by the optical sensor.

Figure 1:
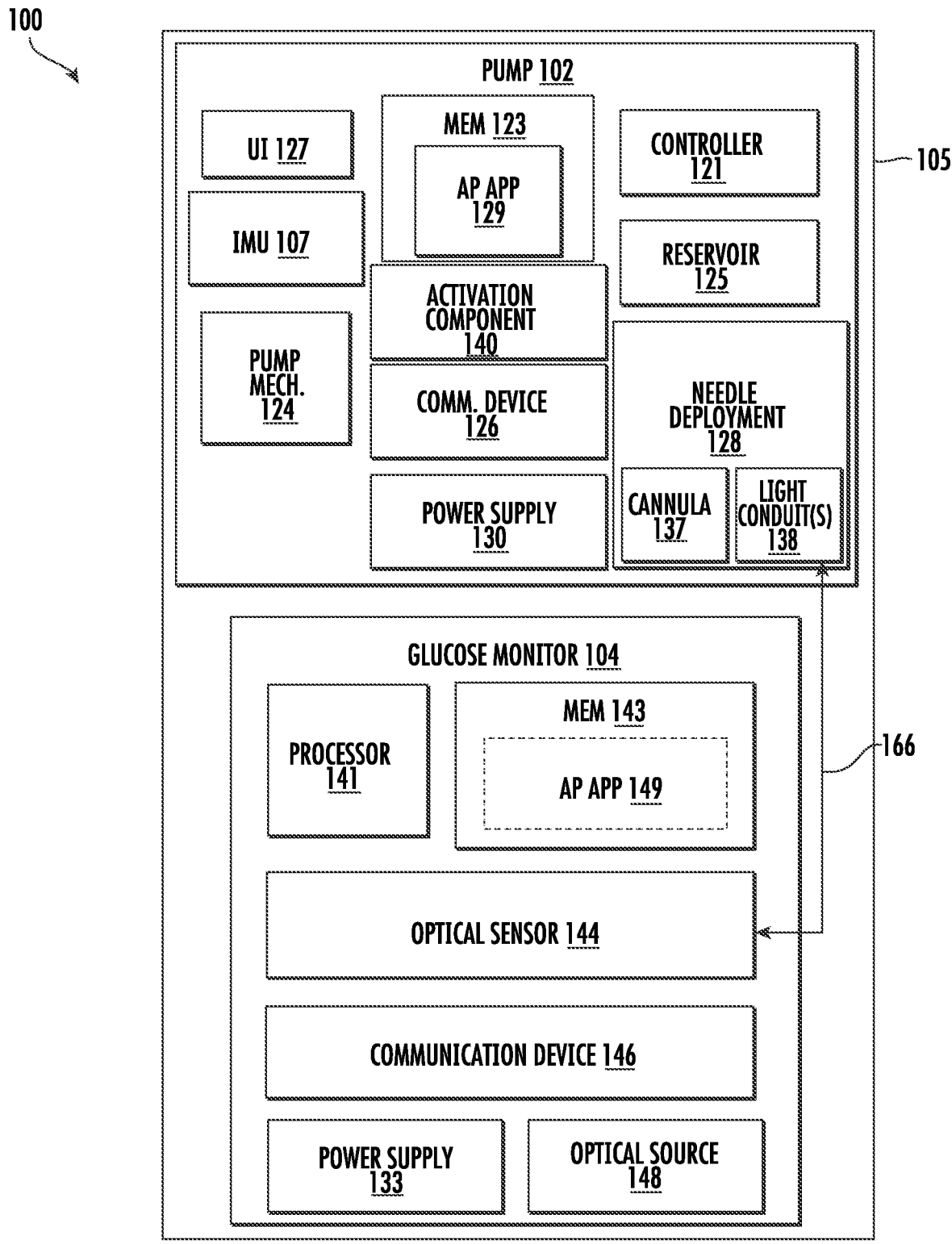
FIG. 1 illustrates an example of a system according to embodiments of the present disclosure.

FIG. 1 illustrates an example of a wearable drug delivery device 100. Various examples of the drug delivery system 100 include a pump 102 that may operate to manage treatment of a diabetic user according to a diabetes treatment plan. The diabetes treatment plan may include a number of parameters related to the delivery of insulin that may be determined and modified in response to patient glucose levels received at a glucose monitor 104, such as a CGM. As shown, the glucose monitor 104 and the pump 102 may be housed within a same outer housing 105 to eliminate the need for the patient to wear two separate devices.

As shown, the pump 102 may include a pump mechanism 124 and a needle deployment component 128. In various examples, the pump mechanism 124 may include a pump or a plunger (not shown), while the needle deployment component 128 may include a needle and/or cannula 137 for communicating a stored liquid drug in a reservoir 125 to the patient. As will be described in greater detail herein, the needle deployment component 128 may further include one or more optical conduits 138 insertable into the patient for detecting blood glucose levels.

The wearable drug delivery device 100 may further include a controller 121 and a communications interface device 126. The controller 121 may be implemented in hardware, software, or any combination thereof. The controller 121 may, for example, be a processor, microprocessor, a logic circuit, or a microcontroller coupled to a memory. The controller 121 may maintain a date and time as well as other functions (e.g., calculations or the like) performed by processors. The controller 121 may be operable to execute an artificial pancreas algorithm (AP app) 129 stored in memory 123 that enables the controller 121 to direct operation of the pump 102. In addition, the controller 121 may be operable to receive data or information from the glucose monitor 104, as well as from any other sensor, such as an inertia motion unit (IMU) 107. As will be described in greater detail below, the controller 121 may be further operable to receive data from the glucose monitor 104 to control delivery of the liquid drug to the patient.

The controller 121 may process the data from the glucose monitor 104 or any other sensor to determine if an alert or other communication is to be issued to the user and/or a caregiver of the user, or if an operational mode of the drug delivery device 100 is to be adjusted. The controller 121 may provide the alert, for example, through the communications interface device 126. The communication link provided by the communications interface device 126 may include any wired or wireless communication link operating according to any known communications protocol or standard, such as RFID, Bluetooth, NFC, or a cellular standard, for example.

In some embodiments, the pump 102 may further include a power supply 130, such as a battery, a piezoelectric device, or the like, for supplying electrical power to the pump mechanism 124 and/or other components of the pump, such as the controller 121, memory 123, the needle deployment component 128, and the communication interface device 126. In some embodiments, the glucose monitor 104 may also include a power supply 133. In some embodiments, power supply 133 and power supply 130 may be the same power supply on drug delivery device 100 such that one power supply powers both the pump 102 and glucose monitor 104.

In some embodiments, the wearable drug delivery device 100 may, when operating in a normal mode of operation, provide insulin stored in reservoir 125 to the user based on information (e.g., blood glucose measurement values, target blood glucose values, insulin on board, prior insulin deliveries, time of day, day of week, inputs from the IMU 107, global positioning system-enabled devices, Wi-Fi-enabled devices, or the like) provided by the glucose monitor 104 or other functional elements on drug delivery device 100. For example, the wearable drug delivery device 100 may contain analog and/or digital circuitry that may be implemented as the controller 121 for controlling delivery of the drug or therapeutic agent. The circuitry used to implement the controller 121 may include discrete, specialized logic and/or components, an application-specific integrated circuit, a microcontroller or processor that executes software instructions, firmware, programming instructions or programming code enabling, for example, the AP App 129 stored in memory 123, or any combination thereof. For example, the controller 121 may execute a control algorithm, such as the AP application 129, and other programming code, that may make the controller 121 operable to cause the pump mechanism 124 to deliver doses of the liquid drug to the patient at predetermined intervals or as needed to bring blood glucose measurement values to a target blood glucose value. Furthermore, the size and/or timing of the doses may be pre-programmed, for example, into the AP application 129 by the user or by a third party (such as a health care provider, a parent or guardian, a manufacturer of the wearable drug delivery device, or the like) using a wired or wireless link.

In some embodiments, the glucose monitor 104 may include a processor 141, a memory 143, a sensing or measuring device, such as an optical sensor 144, and a communication device 146. The memory 143 may store an instance of an AP application 149 as well as other programming code and be operable to store data related to the AP application 149. The optical sensor 144, the processor 141, and the AP application 149 may form an optical system. Although not shown, the optical system may further consist of filters, dichroic elements, beam splitters, polarizers, and/or electronics for signal detection and modulation. The optical sensor 144 may communicate with the processor 141, wherein the processor 141 may include discrete, specialized logic and/or components, an application-specific integrated circuit, a microcontroller or processor that executes software instructions, firmware, programming instructions stored in memory (such as memory 143), or any combination thereof.

As will be described in greater detail herein, the optical sensor 144 may detect/measure a light output 166 received via the optical conduit(s) 138, wherein the light output 166 correlates to a blood glucose measurement or concentration. In some embodiments, the light output 166 is a fluorescent light generated by a glucose binding material, such as a glucose-indicating hydrogel, which is coated or connected to the optical conduit 138 and/or the cannula 137. The glucose monitor 104 may further include an optical source 148 (e.g., LED light source) for delivering light to the patient's tissue using one of the optical conduits 138.

The pump 102 may also include a user interface 127, which may include any mechanism for the user to input data to the pump 102, such as, for example, a button, a knob, a dial, a switch, a touch-screen display, or any other user interaction component. The user interface 127 may include any mechanism for the drug delivery device 100 to relay data to the user and may include, for example, a numbered dial or knob, a display, a touch-screen display, or any means for providing a visual, audible, or tactile (e.g., vibrational) output (e.g., as an alert). The user interface 127 may also include a number of additional components not specifically shown for the sake brevity and explanation. For example, the user interface 127 may include one or more user input/output components for receiving inputs from or providing outputs to a user or a caregiver (e.g., a parent or nurse), a display that outputs a visible alert, a speaker that outputs an audible alert, or a vibration device that outputs tactile indicators to alert a user or a caregiver of a potential activity or operational mode, a power level, and the like. Inputs to the user interface 127 may, for example, be a via a fingerprint sensor, a tactile input sensor, a button, a touch screen display, a switch, or the like. In yet another alternative, changes to the operation of the drug delivery device 100 may be requested through a management device (not shown), such as an app running on a smartphone or smartwatch or other mobile device, that is communicatively coupled to the controller 121.

Figure 2:
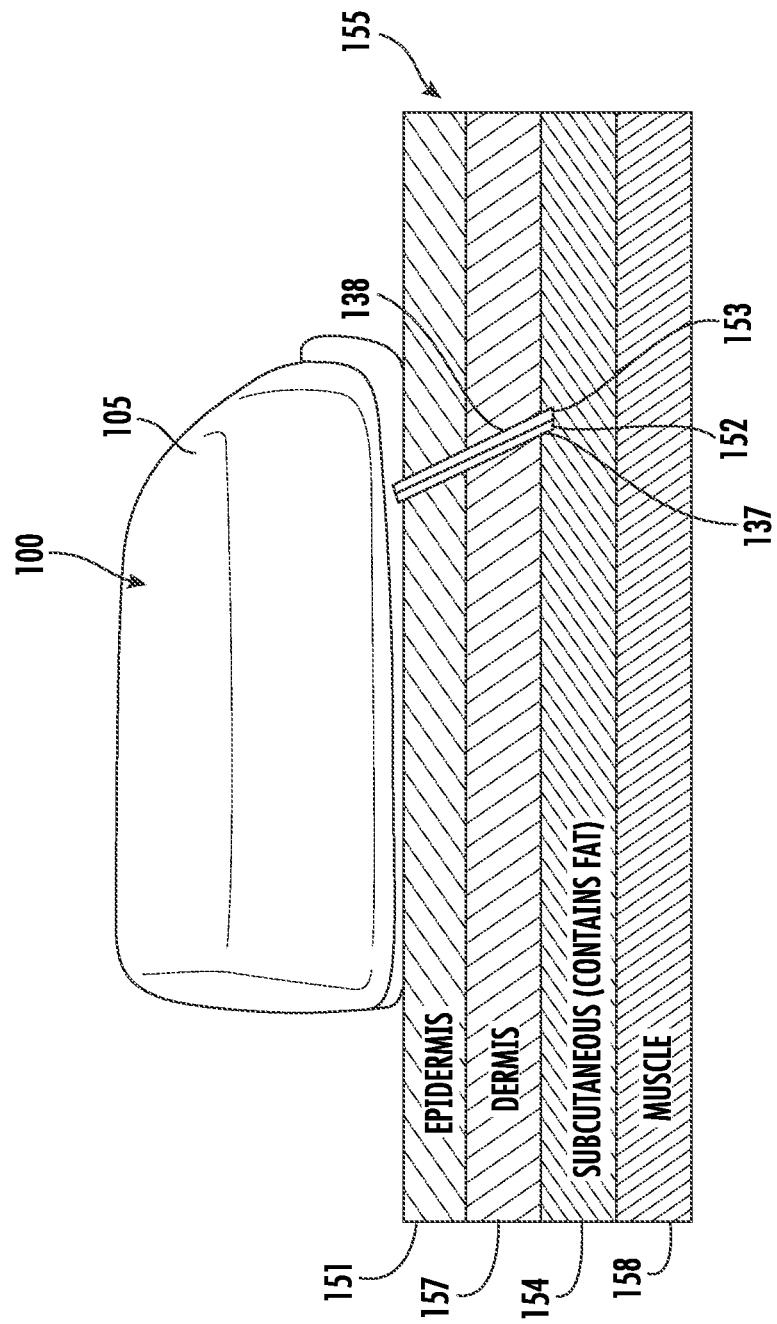
FIG. 2 illustrates an example wearable drug delivery device attached to a user according to embodiments of the present disclosure.

FIG. 2 demonstrates connection of the drug delivery device 100 to a user 155 according to embodiments of the present disclosure. For simplicity, only the outer housing 105, the cannula 137, and a single optical conduit 138 are shown. The drug delivery device 100 may be attached to an epidermis layer 151 of the user 155 by an adhesive layer. During operation, the cannula 137 and the optical conduit 138 are deployed either simultaneously or sequentially into the user 155. In some embodiments, the cannula 137 and the optical conduit 138 are directly coupled to one another, causing the cannula and the optical conduit 138 to move together. As shown, a first end 152 of the cannula 137 and a first end 153 of the optical conduit 138 generally extend to a same depth, e.g., into a subcutaneous tissue layer 154. In other embodiments, the first end 152 of the cannula 137 and the first end 153 of the optical conduit 138 extend to different depths such that a drug expelled out of cannula 137 does not interfere with a glucose reading by the optical conduit 138. Furthermore, in various other embodiments, the first end 152 of the cannula 137 and/or the first end 153 of the optical conduit 138 may terminate in a dermis tissue layer 157 or a muscle tissue layer 158.

Figure 3:
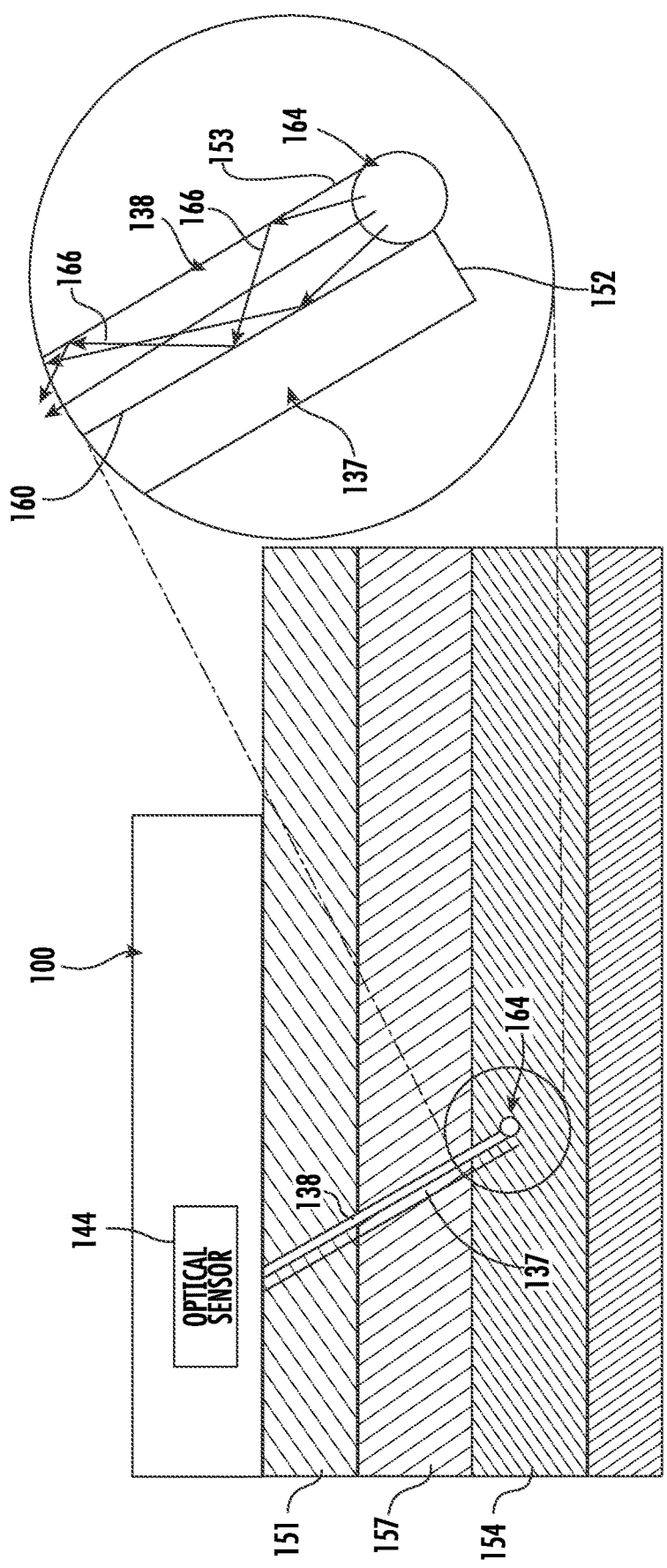
FIG. 3 depicts a cannula and an optical conduit according to embodiments of the present disclosure.

Referring to FIG. 3, the cannula 137 and the optical conduit 138 according to embodiments of the present disclosure will be described in greater detail. As shown, the cannula 137 and the optical conduit 138 of the drug delivery device 100 are coupled together and deployed into the subcutaneous tissue layer 154. The first or distal end 152 of the cannula 137 and the first or distal end 153 of the optical conduit 138 extend through the epidermis layer 151 and the dermis tissue layer 157, terminating in the subcutaneous tissue layer 154. Although not shown, a second or proximal end of the optical conduit 138 may terminate within a housing or chamber of the optical sensor 144.

In this embodiment, the optical conduit 138 may be coupled or otherwise secured to an exterior 160 of the cannula 137. In other embodiments, the optical conduit 138 may be at least partially contained within the cannula 137. In yet other embodiments, the optical conduit 138 may be contained within a separate tube or housing (not shown), which may be attached to the cannula 137. The optical conduit 138, which may vary in length, delivers light into the optical sensor 144. Although non-limiting, the optical conduit 138 may be a lens, a reflective channel, a needle, or an optical fiber. The optical fiber may be either a single strand of optical fiber (single or multimode) or a bundle of more than one fiber. In some embodiments, the bundle of fibers may be bifurcated. The optical conduit 138 may be non-tapered or tapered for easier penetration through the epidermis layer 151 of the user 155, as may be a distal end of cannula 137.

As further shown, a glucose binding material 164 may be coupled to or coated on the first end 153 of the optical conduit 138. In some embodiments, the glucose binding material 164 may additionally or alternatively be disposed on the cannula 137. In some embodiments, the glucose binding material may be a fluorescent, boronic acid-based glucose indicating polymer or hydrogel. Although non-limiting, the hydrogel may be poly(ethylene glycol) (PEG), poly(vinyl alcohol) (PVA), poly(N-vinyl pyrrolidone) (PVP), or poly(hydroxy ethylmethacrylate) (PHEMA). The hydrogel may also come from the group consisting of ePTFE, polyurethane, silicone rubber, cross-linked collagen, polypropylene, cellulose acetate, poly(vinylidene fluoride) (PVDF), Nafion or other biocompatible material. In one embodiment, the glucose-indicating hydrogel may consist primarily of poly(2-hydroxyethylmethacrylate) (pHEMA) into which a fluorescent indicator (e.g., boronic acids groups) is copolymerized. The glucose reversibly binds to the indicator, which acts as a glucose receptor in an equilibrium binding reaction. Subsequent disruption of photo induced electron transfer (PET) results in an increased fluorescence light intensity upon binding of glucose. The fluorescent light, or light output 166, is then transmitted via the optical conduit 138 back to the optical sensor 144. A change in the wavelength, intensity, lifetime, energy transfer efficiency, and/or polarization of the luminescence of the light output 166 can be processed and interpreted to determine a corresponding change in glucose concentration of the subcutaneous tissue layer 154.

Figure 4:
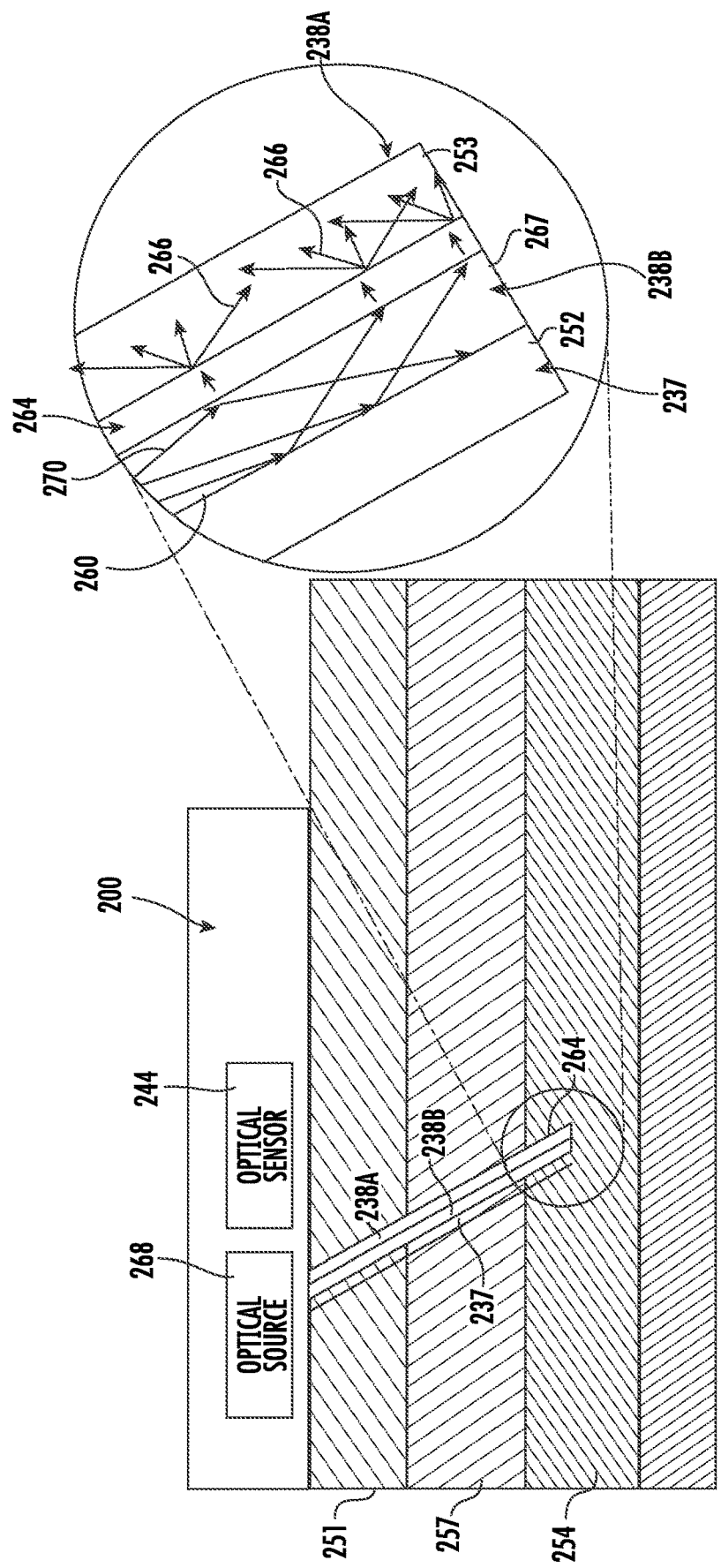
FIG. 4 depicts a cannula and one or more optical conduits according to embodiments of the present disclosure.

Referring to FIG. 4, a wearable drug delivery device 200 according to embodiments of the present disclosure is shown. The wearable drug delivery device 200 may include many or all of the same components and features of the wearable drug delivery device 100 described above. As such, only certain aspects of the wearable drug delivery device 200 will hereinafter be described for the sake of brevity. As shown, the wearable drug delivery device 200 may include a cannula 237, a first optical conduit 238A, and a second optical conduit 238B. The cannula 237, the optical conduit 238A, and the second optical conduit 238B may be coupled or fixed together and deployed into a subcutaneous tissue layer 254. A first end 252 of the cannula 237, a first end 253 of the optical conduit 238A, and a first end 267 of the second optical conduit 238B may generally extend to a same depth, e.g., in the subcutaneous tissue layer 254. In other embodiments, the cannula 237, the optical conduit 238A, and the second optical conduit 238B may be different lengths. Although not shown, a second or proximal end of the optical conduit 238A may terminate within a housing or chamber of an optical sensor 244, while a second or proximal end of the second optical conduit 238B may terminate proximate an optical source 268 (e.g., LED light source). The optical conduit 238A delivers light into the optical sensor 244, while the second optical conduit 238B delivers light from the optical source 268 towards the first end 267 thereof. Although non-limiting, the optical conduit 238A and the second optical conduit 238B may each include one or more optical fibers.

In this embodiment, the optical conduit 238A and the second optical conduit 238B may be coupled or otherwise secured to an exterior 260 of the cannula 237. In other embodiments, the first and second optical conduits 238A, 238B may be at least partially contained within the cannula 237. In yet other embodiments, the first and second optical conduits 238A, 238B may be contained within one or more separate tubes (not shown). The optical conduit 238A and the second optical conduit 238B may be non-tapered or tapered for easier penetration through an epidermis layer 251, as may be a distal end of cannula 237.

As further shown, a glucose binding material 264 may be disposed between the optical conduit 238A and the second optical conduit 238B. The glucose binding material 264 may be a layer extending entirely or partially along a length of the optical conduit 238A and the second optical conduit 238B. In some embodiments, the glucose binding material 264 may be a fluorescent, boronic acid-based glucose indicating polymer or hydrogel, which fluoresces in the presence of glucose. The glucose binding material 264 may further fluoresce in response to a light input 270 from the optical source 268, which acts as an excitation source. For example, the light input 270 may improve luminescence and/or amplify the return signal of a light output 266. The fluorescent light, or light output 266, is then transmitted via the optical conduit 238 back to the optical sensor 244 for further processing and interpretation. A wavelength, intensity, lifetime, energy transfer efficiency, and/or polarization of the luminescence of the light output 266 indicates a corresponding glucose concentration. For example, a higher intensity of light output 266 may indicate a higher concentration of glucose bound to glucose binding material 264. Hence, the light output 266 may be used to determine a glucose concentration in the subcutaneous space, and such glucose concentrations may be determined regularly over time, for example, every 5 minutes, to determine changes or a trend in glucose concentration over time. These concentrations or trends in concentrations may be used to indicate how much insulin should be delivered via cannula 237 now or in the future.

Figure 5:
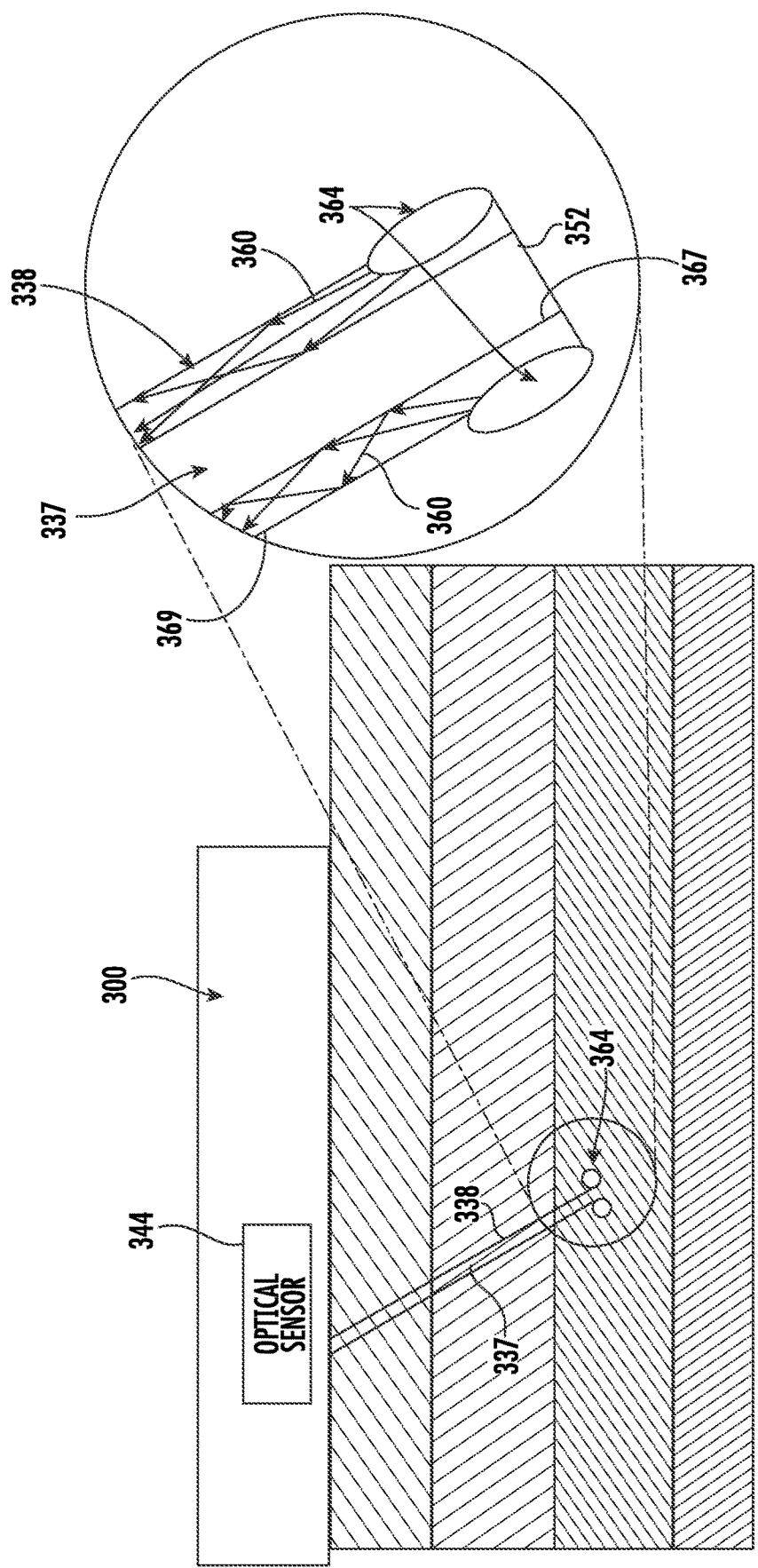
FIG. 5 depicts a cannula system according to embodiments of the present disclosure.

Referring to FIG. 5, a wearable drug delivery device 300 according to embodiments of the present disclosure is shown. The wearable drug delivery device 300 may include many or all of the same components and features of the wearable drug delivery devices 100 and 200 described above. As such, only certain aspects of the wearable drug delivery device 300 will hereinafter be described for the sake of brevity. As shown, the wearable drug delivery device 300 may include a cannula 337 having a cylindrical wall 338 that functions as an optical conduit to deliver a light output 360 to an optical sensor 344. Although non-limiting, the cylindrical wall 338 may be made from a glass material, such as a silica-based material, having an index of refraction to deliver the light output 360 between an inner surface 367 and an outer surface 369 of the cylindrical wall 338.

As further shown, a glucose binding material 364 may be coupled to or coated on a first end 352 of the cannula 337. For example, the glucose binding material 364 may be coated or attached to the outer surface 369 of the cylindrical wall 338. In some embodiments, the glucose binding material may be a fluorescent, boronic acid-based glucose indicating polymer or hydrogel. The fluorescent light, or light output 360, is then transmitted via the cylindrical wall 338 back to the optical sensor 344. A change in the wavelength, intensity, lifetime, energy transfer efficiency, and/or polarization of the luminescence of the light output 366 can be processed and interpreted to determine a corresponding change in glucose concentration, as explained above.

Figure 6:
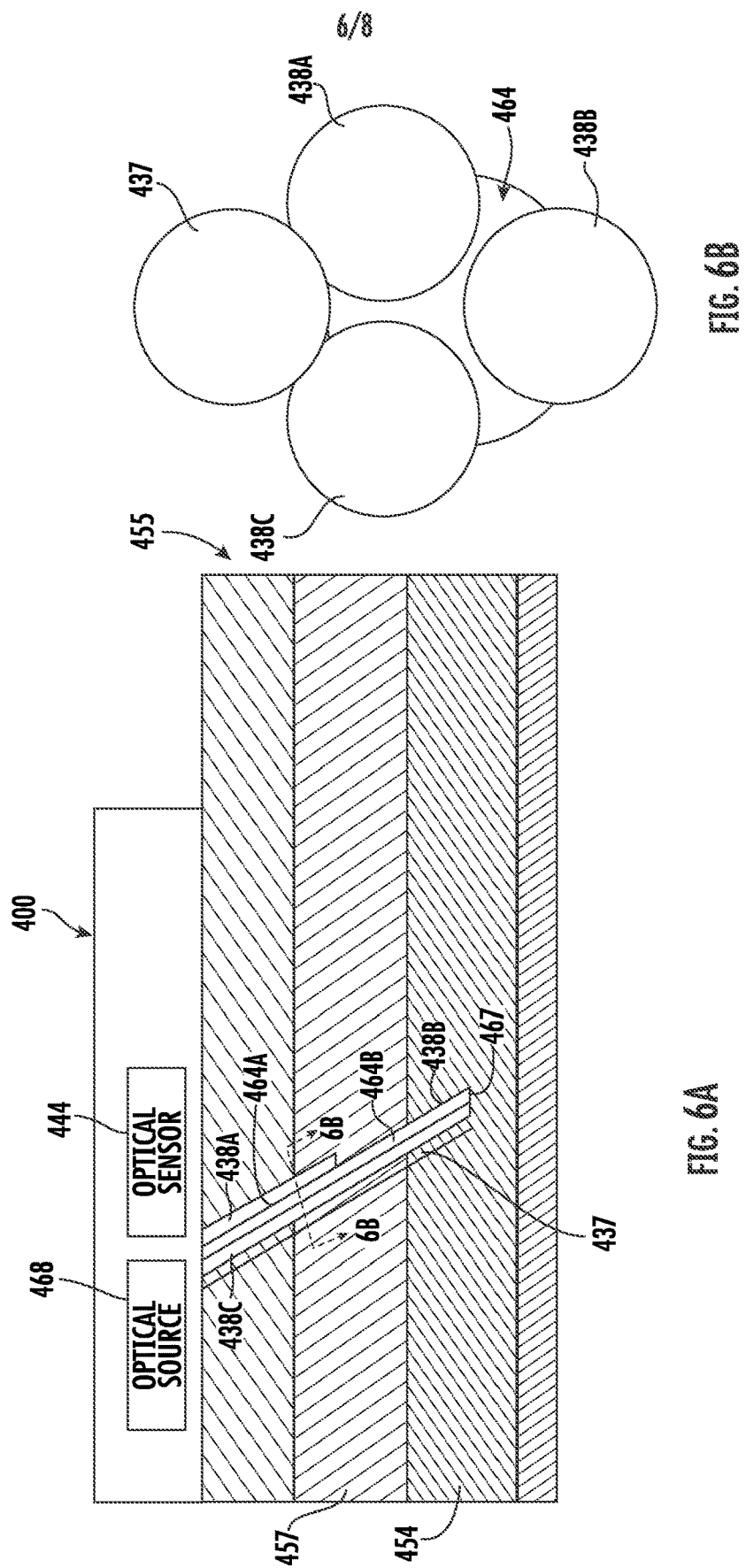
FIGS. 6A-6B depict a cannula and a plurality of optical conduits according to embodiments of the present disclosure.

Referring to FIGS. 6A-6B, a wearable drug delivery device 400 according to embodiments of the present disclosure is shown. The wearable drug delivery device 400 may include many or all of the same components and features of the wearable drug delivery devices 100, 200, and 300 described above. As such, only certain aspects of the wearable drug delivery device 400 will hereinafter be described for the sake of brevity. As shown, the wearable drug delivery device 400 may include a cannula 437, an optical conduit 438A, a second optical conduit 438B, and a third optical conduit 438C. The cannula 437 and the optical conduits 438A-438C may be coupled or fixed together and deployed into a user 455. For example, the optical conduit 438A may extend into and terminate in a dermis tissue layer 457, while the second and third optical conduits 438B, 438C may extend into and terminate in a subcutaneous tissue layer 454. In this embodiment, the optical conduit 438A and the third optical conduit 438C deliver light to an optical sensor 444, while the second optical conduit 438B delivers light from an optical source 468 towards a first end 467 thereof. Although non-limiting, the optical conduits 438A-438C may be optical fibers.

As further shown, a glucose binding material 464 may be disposed between the optical conduits 438A-438C. In some embodiments, the glucose binding material 464 may include a first layer 464A extending entirely or partially along a length of the optical conduit 438A, and a second layer extending entirely or partially along a length of the optical conduits 438B, 438C. For example, glucose binding material 464 may be positioned around a distal end of optical conduits 438A, 438B, and 438C. In some embodiments, the glucose binding material 464 may be a fluorescent, boronic acid-based glucose indicating polymer or hydrogel, which fluoresces in the presence of glucose. The glucose binding material 464 may fluoresce in response to a light input from the optical source 468, which acts as an excitation source. For example, the light input may improve luminescence and/or amplify the return signal of a first light output traveling through the optical conduit 438A and a second light output traveling through the third optical conduit 438C. The fluorescent light outputs are transmitted back to the optical sensor 444 for further processing and interpretation. A wavelength, intensity, lifetime, energy transfer efficiency, and/or polarization of the luminescence of the first and second light outputs indicates a corresponding glucose concentration.

In this embodiment, the optical sensor 444 may advantageously sense glucose at two different biological tissue layers, e.g., the dermis tissue layer 457 and the subcutaneous tissue layer 454. The subcutaneous tissue layer 454 and the dermis tissue layer 457 have different rates of response to glucose changes, as the dermis tissue layer 457 generally reflects glucose changes faster than the subcutaneous tissue layer 454. By measuring both at the same time, glucose trends can be determined from a single snapshot in time as opposed to waiting for multiple measurements over a longer period of time from a single layer of the tissue. In some embodiments, the optical sensor 444 can include multiple optical sensors, one for each of optical conduits 438A, 438C. Furthermore, more than one optical source 468 may be employed in the case more than one optical conduit is present. Each optical source may feed light into one or more of the optical conduits 438A, 438C. In various embodiments, each of the optical sources may be the same or different. For example, the type of optical source may differ (e.g., LED, Infrared, ultraviolet, fluorescent) and/or one or more light characteristics may differ (e.g., color, intensity, propagation direction, frequency or wavelength, polarization, etc.) across the different optical sources. Embodiments herein are not limited in this context.

Figure 7:
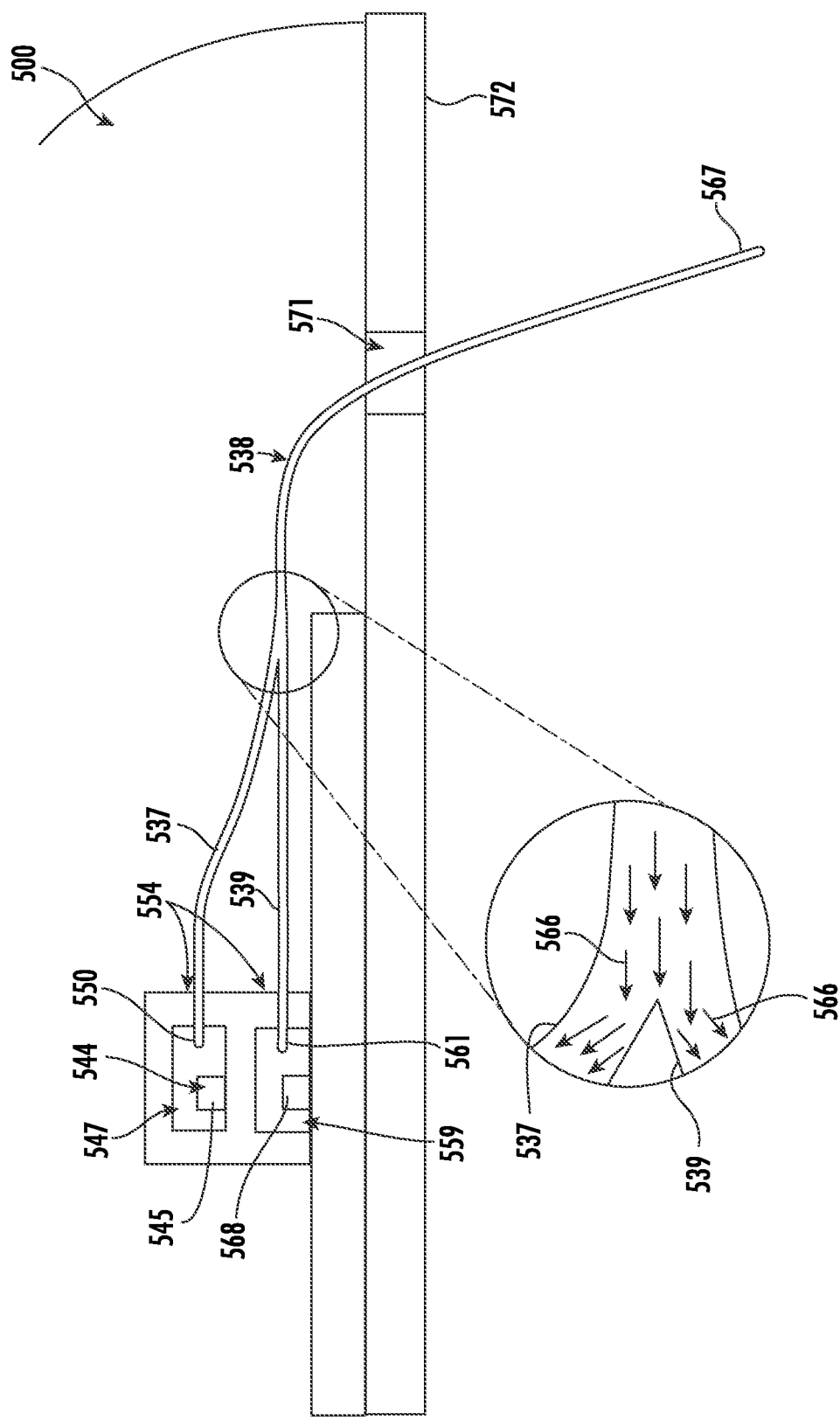
FIG. 7 depicts an optical sensor and an optical source according to embodiments of the present disclosure.

Turning now to FIG. 7, an optical sensor 544 and an optical source 568 of a wearable drug delivery device 500 according to embodiments of the present disclosure will be described. In the embodiment shown, an optical conduit 538 may be bifurcated into a first portion 537 and a second portion 539. The optical conduit 538 may deliver a light output 566 from a tissue end 567 to the optical sensor 544, along the first portion 537. The light output 566 delivered along the second portion 539 will have little effect. Instead, the second portion 539 is operable to deliver a light input (not shown) from the optical source 568 towards the tissue end 567.

In other embodiments, multiple optical conduits may be present. For example, as described above with respect to FIGS. 4, 6A, and 6B, at least one of the optical conduits may deliver the light output 566 from the tissue end 567 to the optical sensor 544, while a separate optical conduit may deliver a light input from the optical source 568 towards the tissue end 567.

The optical sensor 544 may include one or more photodiodes 545 positioned within a first chamber 547. In the case multiple optical conduits are delivering light inputs from the tissue end 567 to the optical sensor 544, multiple photodiodes each located in a separate chamber may be provided. The photodiode 545 may be a spectrally filtered photodiode, which measures the glucose-dependent fluorescence intensity of the light output 566 at a second end 550 of the optical conduit 538. As shown, the second end 550 of the optical conduit 538 may extend through a wall 554 of the first chamber 547, terminating proximate the photodiode 545.

The optical source 568 may be located within a second chamber 559. Although non-limiting, the optical source 568 may include a variety of illumination sources, such as one or more LEDs 568, positioned in optical proximity to a second end 561 of a second portion 539 of the optical conduit 538. As used herein, "optical proximity" means that components are close enough to one another such that an optical signal can be transmitted to or received from one object by another. The photodiode 545 may be placed in optical proximity to the second end 550 of the optical conduit 538 in a number of ways, for example, secured to the wall 554 of the first chamber 547, attached directly to the second end 550 of the optical conduit 538, attached to a connector that is attached to the optical conduit 538, etc. The photodiode 545 may be permanently affixed to the optical conduit 538 or replaceably attached such that the photodiode 545 can be replaced conveniently and economically. The second end 561 of the second portion 539 of the optical conduit 538 may similarly be attached to the LED 568 in a variety of ways. Embodiments herein are not limited in this context. As further shown, the optical conduit 538 may pass through a seal 571 along a base 572 of the wearable drug delivery device 500. Although not shown, the optical conduit 538 may be coupled to a cannula to allow the cannula and the optical conduit 538 to be deployed together, as described herein.

During operation, the optical source 568 sends light down the optical conduit 538 for a period of time (e.g, 0.1 second, 1 second, 3 seconds, 5 seconds, etc.) and at a given frequency (e.g., 5 MHz), then shuts off for a second period of time. In the case a glucose binding material is present at the tissue end 567 of the optical conduit 538, the light from the optical source 568 can induce or amplify luminescence at the glucose binding material. Because glucose tends to bind to the glucose binding material (e.g., hydrogel), subsequent disruption of photo induced electron transfer (PET) results in an increased fluorescence light intensity upon binding of glucose. In other embodiments, no glucose binding material is present, and the fluorescence of glucose may be monitored directly.

After the optical source 568 is turned off, the light output 566 returns along the optical conduit 538 to be sensed by the optical sensor 544. The luminescent properties of the light output 566, such as wavelength, intensity, lifetime, energy transfer efficiency, or polarization, change in response to binding or unbinding of the glucose to/from the glucose binding material. These luminescent changes may be detected by the optical sensor 544 and returned to the processor 141 of the glucose monitor 104 (FIG. 1) to determine the concentration of glucose in the body or subdermal space of the user. For example, a given luminance intensity may correspond to a voltage or current across electrodes of the optical sensor 544, which may vary directly with the level or concentration of glucose. Detected voltage/current levels may then be used to determine if the level, rate of change, and/or acceleration in the rate of change of the glucose concentration exceeds or meets one or more threshold values. In some embodiments, an alarm or trigger output may be activated if a threshold value is met or exceeded. The on/off cycle from the optical source 568 may run periodically to evaluate trends in or values of the level of the glucose concentration based on a series of sensor signals, and to determine medication dosing recommendations. In other words, as the trends in or values of the glucose concentration are detected using any of the various embodiments disclosed herein, these trends or values may be input to the artificial pancreas (AP) app 129 to calculate insulin dosing values (e.g., basal and/or bolus dosage amounts) and timing of delivery of such insulin dosing, and each insulin dosing may be delivered by the drug delivery device (100, 200, 300, 400). In this manner the glucose monitor 104 and pump 102 may operate in a closed-loop fashion by detecting glucose concentrations, calculating requisite insulin dosage amounts to bring the glucose concentration to a target or within a euglycemic zone, and deliver the insulin at the appropriate dosage amount and timing to achieve an optimal time in range within the euglycemic zone.

The various components of the drug delivery device 500 may also be incorporated into drug delivery devices 100, 200, 300, 400 described above and shown in the figures. Although non-limiting, the first chamber 547, the second chamber 559, the optical sensor 544, and the optical source 568 may be present in any of drug delivery devices 100, 200, 300, 400.

Figure 8:
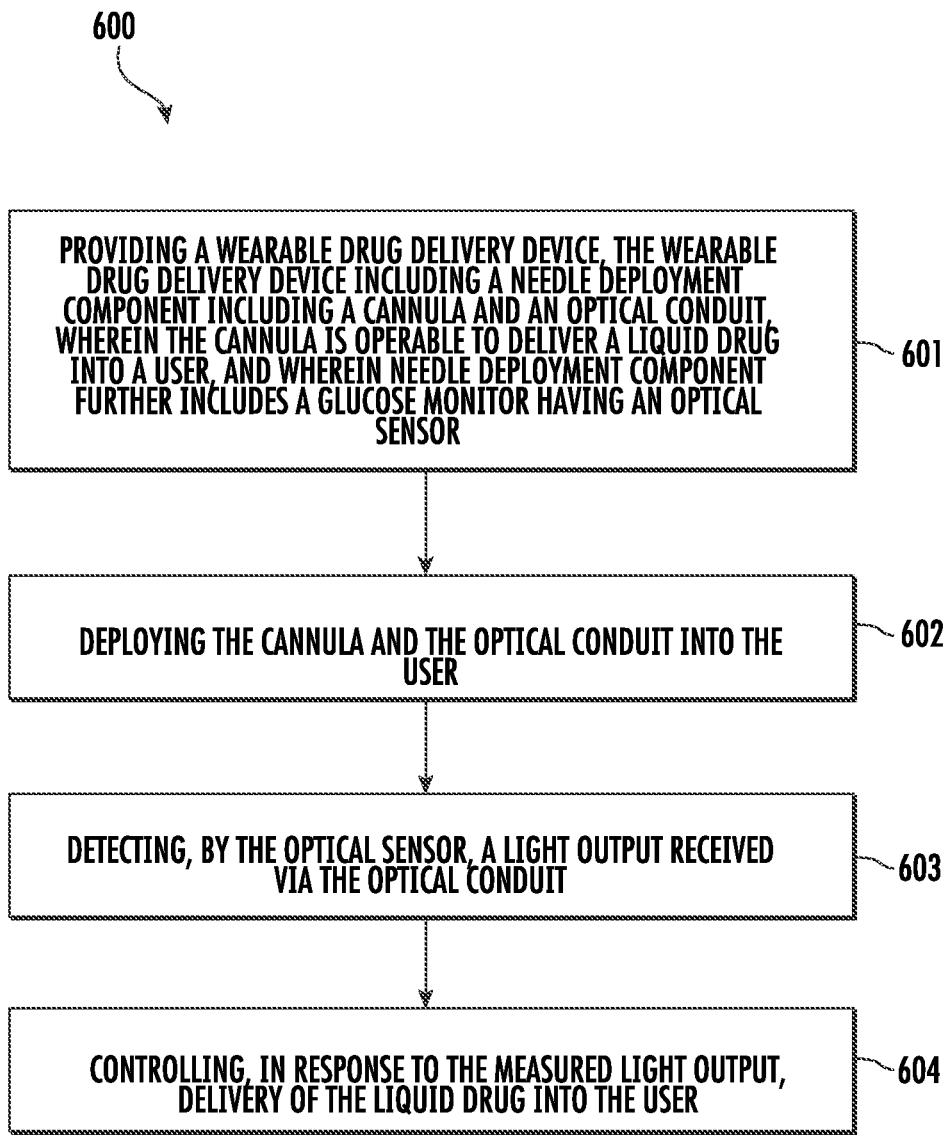
FIG. 8 illustrates a process flow according to embodiments of the present disclosure.

FIG. 8 illustrates an example process 600 implemented by one or more of the wearable drug delivery devices described herein. At block 601, the process 600 may include providing or obtaining a wearable drug delivery device, the wearable drug delivery device including a needle deployment component including a cannula and an optical conduit, wherein the cannula is operable to deliver a liquid drug into a user, and wherein needle deployment component further includes a glucose monitor having an optical sensor. In some embodiments, the cannula and the optical conduit are directly coupled together.

At block 602, the process 600 may further include deploying the cannula and the optical conduit into the user. In some embodiments, the cannula and the optical conduit are deployed simultaneously. In some embodiments, a first end of the optical conduit may be inserted into a subcutaneous tissue layer of the user, while a second end of the optical fiber is positioned optically proximate the optical sensor. In some embodiments, the process may further include deploying a second optical conduit into the user, and delivering, via the second optical conduit, a light input from an optical source to the second end of the optical conduit. The light input from the optical source may act as an excitation source to improve luminescence and/or amplify the return signal of the light output. In some embodiments, the process may further include deploying a third optical conduit into the user, wherein a first end of the third optical conduit terminates in a dermis tissue layer, for example. When a third optical conduit is deployed, the optical sensor may simultaneously sense glucose at two different biological tissue layers, e.g., the dermis tissue layer and the subcutaneous tissue layer.

At block 603, the process 600 may further include detecting, by the optical sensor, a light output received via the optical conduit. In some embodiments, the process may include connecting a glucose binding material to at least one of the cannula and the optical conduit, the glucose binding material adapted to generate the light output in response to glucose within the user binding to the glucose binding material and photochemically exciting photons. In some embodiments, the glucose binding material may be positioned between the optical conduit and the second optical conduit. In some embodiments, the process may further include coating a surface of the optical conduit with the glucose binding material, wherein the glucose binding material is a glucose-indicating hydrogel operable to generate a fluorescent light, and detecting the fluorescent light using a photodiode of the optical sensor.

At optional block 604, the process 600 may include controlling delivery of the liquid drug into the user based on the measured light output. For example, insulin delivery can be increased or decreased in response to different levels of glucose concentration detected. For example, a higher intensity of light output may indicate a higher concentration of glucose bound to glucose binding material. Hence, the light output may be used to determine a glucose concentration in the subcutaneous space, and such glucose concentrations may be determined regularly over time, for example, at least every 5 minutes, to determine changes or a trend in glucose concentration over time. These concentrations or trends in concentrations may be used to indicate how much insulin should be delivered to a patient using the wearable drug delivery device as a bolus or basal delivery of insulin. And depending on the changes in concentration of glucose, the bolus or basal amounts of insulin delivered may be modified over time based on such changes in concentrations.

The techniques described herein for a drug delivery system or device (e.g., the devices 100, 200, 300, 400, 500, or any components thereof) may be implemented in hardware, software, or any combination thereof. Any component as described herein may be implemented in hardware, software, or any combination thereof. For example, the system 100 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:
   a needle deployment component including a cannula and an optical conduit deployable into a user, the cannula operable to deliver a liquid drug to the user;
   a glucose monitor including an optical sensor, the optical sensor operable to measure a light output received via the optical conduit; and
   a glucose binding material connected to at least one of the cannula and the optical conduit, wherein the glucose binding material generates the light output in response to glucose.

2. The wearable drug delivery device of claim 1, wherein the optical conduit comprises an optical fiber, wherein a first end of the optical fiber is insertable into a subcutaneous tissue layer of the user, and wherein a second end of the optical fiber is positioned proximate the optical sensor.

3. The wearable drug delivery device of claim 1, wherein the glucose monitor is a continuous glucose monitor (GGM), and wherein the CGM and the needle deployment component are located within a same outer housing.

4. The wearable drug delivery device of claim 1, wherein the glucose binding material is a glucose-indicating hydrogel coating a surface of the optical conduit, and wherein the light output is a fluorescent light.

5. The wearable drug delivery device of claim 4, wherein the optical sensor comprises a photodiode operable to detect a fluorescence intensity of the fluorescent light.

6. A wearable drug delivery device, comprising:
   a needle deployment component including a cannula and first optical conduit deployable into a user, the cannula operable to deliver a liquid drug to the user;
   a glucose monitor including an optical sensor, the optical sensor operable to measure a light output received via the optical conduit, wherein the first optical conduit comprises a first optical fiber, wherein a first end of the first optical fiber is insertable into a subcutaneous tissue layer of the user, and wherein a second end of the optical fiber is positioned proximate the optical sensor; and a second optical conduit comprising a second optical fiber with a first end that is insertable into a subcutaneous tissue layer of the user and a second end that is positioned proximate the optical sensor, the second optical conduit operable to deliver a light input from an optical source to the second end of the optical fiber.

7. The wearable drug delivery device of claim 6, wherein the glucose binding material is positioned between the first optical conduit and the second optical conduit.

8. The wearable drug delivery device of claim 6, further comprising a third optical conduit, wherein a first end of the third optical conduit terminates in a dermis tissue layer when the first optical conduit, the second optical conduit, and the third optical conduit are inserted into the user.

9. The wearable drug delivery device of claim 8, wherein the glucose binding material extends along a length of each of the optical conduit, the second optical conduit, and the third optical conduit.

10. A method, comprising:
    providing a wearable drug delivery device, the wearable drug delivery device comprising: a needle deployment component including a cannula and an optical conduit, the cannula operable to deliver a liquid drug into a user; and a glucose monitor including an optical sensor;
    connecting a glucose binding material to at least one of the cannula and the optical conduit, wherein the glucose binding material generates the light output in response to glucose within the user;
    deploying the cannula and the optical conduit into the user; and
    detecting, by the optical sensor, a light output received via the optical conduit.

11. The method of claim 10, further comprising: coupling together the cannula and the optical conduit; and simultaneously deploying the cannula and the optical conduit into the user.

12. The method of claim 10, further comprising controlling, in response to the light output, delivery of the liquid drug into the user.

13. The method of claim 10, further comprising: coating a surface of the optical conduit with the glucose binding material, wherein the glucose binding material is a glucose-indicating hydrogel operable to generate a fluorescent light; and detecting the fluorescent light using a photodiode of the optical sensor.

14. The method of claim 10, further comprising deploying a third optical conduit into the user, wherein a first end of the third optical conduit terminates in a dermis tissue layer.

15. The method of claim 10, further comprising: inserting a first end of the optical conduit into a subcutaneous tissue layer of the user; and positioning a second end of the optical conduit optically proximate the optical sensor.

16. The method of claim 15, further comprising: deploying a second optical conduit into the user; and delivering, via the second optical conduit, a light input from an optical source to the second end of the optical conduit.

17. The method of claim 16, further comprising: positioning the glucose binding material between the optical conduit and the second optical conduit.

18. A wearable drug delivery device, comprising:
a needle deployment component including a cannula and an optical conduit coupled together, the cannula operable to deliver a liquid drug into a user;
a glucose monitor including an optical sensor, wherein the optical sensor is operable to measure a light output received via the optical conduit, and wherein the needle deployment component and the glucose monitor are located within a same outer housing; and
a second optical conduit operable to deliver a light input from an optical source to a second end of the optical conduit, wherein the optical conduit comprises an optical fiber, wherein a first end of the optical fiber is insertable into a subcutaneous tissue layer of the user, and wherein the second end of the optical fiber is positioned within a chamber housing a photodiode of the optical sensor.

19. The wearable drug delivery device of claim 18, further comprising a third optical conduit, wherein a first end of the third optical conduit terminates in a dermis tissue layer when the optical conduit, the second optical conduit, and the third optical conduit are inserted into the user.

20. The wearable drug delivery device of claim 18, further comprising a glucose-indicating hydrogel connected to at least one of the cannula and the optical conduit, wherein the glucose-indicating hydrogel generates a fluorescent light in response to glucose.

* * * * *